United States Patent [19]

Grim

[11] Patent Number: 4,844,094
[45] Date of Patent: Jul. 4, 1989

[54] ANKLE BRACE

[75] Inventor: Tracy E. Grim, Tulsa, Okla.

[73] Assignee: Royce Medical Company, Culver City, Calif.

[21] Appl. No.: 55,711

[22] Filed: May 29, 1987

[51] Int. Cl.⁴ .............................................. A61F 3/00
[52] U.S. Cl. .................................. 128/80 H; 128/166
[58] Field of Search ................ 128/80, 80 H, 80 C, 128/80 E, 80 F, 80 G, 80 A, 80 B, 80 D, 68.1, 82.1, 166, 402, 403

[56] References Cited

U.S. PATENT DOCUMENTS

| | | | |
|---|---|---|---|
| 1,340,700 | 5/1920 | Dahl | 128/80 J |
| 3,548,420 | 12/1970 | Spence | 128/83 |
| 4,323,058 | 4/1982 | Detty | 128/80 H |
| 4,572,169 | 2/1986 | Mauldin et al. | 128/80 H |
| 4,628,945 | 12/1986 | Johnson | 128/80 H |

FOREIGN PATENT DOCUMENTS 0068612  1/1983  European Pat. Off. ............ 128/82.1

Primary Examiner—Edgar S. Burr
Assistant Examiner—Huong Q. Pham
Attorney, Agent, or Firm—Poms, Smith, Lande & Rose

[57] ABSTRACT

An ankle brace for insertion into a shoe with laces for immobilizing the ankle against inversion or eversion while permitting planter-flexion and dorsi-flexion, includes, a pair of side supports for fitting about the lower leg on both sides. The side supports have a configuration to encase both sides of the ankle and with the lower end of the side supports for insertion into the sides of the shoe. Pad members are formed of a dense flexible material located on the inner surface of each side support to form a cushion between the ankle and the side supports. The side supports are secured to firmly encase the ankle and lower leg and includes a counter strap extending between the side supports at a lower position just above the heel and a fastener located on the side supports to receive the laces of the shoe so that the laces can be tightened and tied to immobilize the ankle against inversion or eversion or anterior subluxation while permitting planter-flexion and dorsi-flexion.

11 Claims, 3 Drawing Sheets

ANKLE BRACE

BACKGROUND OF THE INVENTION

1. Field of the Invention

The present invention relates to an orthopedic device, and specifically, to an ankle brace for stabilizing an ankle before and after injury. In particular, the ankle brace of the present invention stabilizes the ankle against inversion and eversion and anterior subluxation while allowing normal dorsi-flexion and planter-flexion movement.

2. Background of the Prior Art

After injury to an ankle, such as a fracture or severe ankle sprain, it may be necessary to completely immobilize the ankle through the use of a molded plaster or resin cast. However, once the injury has been stabilized, recovery may be hastened by removing the molded plaster or resin cast and using a removable functional walking brace so that the ankle can be exercised during healing. Also, if the injury is not severe enough to require complete immobilization, it may only be necessary to use a functional walking brace to stabilize the ankle against inversion and eversion while still permitting the normal dorsi-flexion and planter-flexion movement of the ankle.

One such type of walking cast is shown in prior U.S. Pat. No. 4,280,489 listing Glenn W. Johnson Jr. as the inventor. The walking cast shown in the Johnson patent does permit substantially normal dorsi-flexion and planto-flexion movements of the ankle, but limits inversion and eversion to thereby stabilize the ankle. This prior art device is removable and is also adjustable to conform to the ankle.

Unfortunately, the prior art walking brace shown in Johnson U.S. Pat. No. 4,280,489 does not sufficiently immobilize the ankle against inversion and eversion. This is because the prior art Johnson device allows a certain amount of flexture of the brace members in an outward direction so that the ankle may not be sufficiently stabilized against inversion and eversion. In addition, the prior art walking brace shown in the Johnson U.S. Pat. No. 4,280,489 is limited to the use of an air filled bladder or liner to provide a resilient support against the ankle. Such an air filled bladder may also allow for greater movement of the ankle than desired which again would not provide for sufficient stabilization of the ankle against inversion and eversion.

SUMMARY OF THE INVENTION

The present invention overcomes the deficiencies of the prior art as exemplified by the Johnson U.S. Pat. No. 4,280,489 and also includes a U-shaped stirrup member having a base portion and a pair of opposed side wall portions attached to the base portion. In place of the air inflatable liners or air bags of the prior art, the present invention preferably uses liners constructed of a firm dense material such as a gel material so as to provide for a more complete immobilization of the ankle against inversion and eversion while still providing for comfort. The gel material also has the advantage that it may have thermal properties so that the gel may be heated or cooled and with the gel material retaining the heat or cold for a sufficient period of time so that the gel provides for a therapeutic effect.

The present invention also includes a plurality of straps to maintain the side wall portions of the U-shape stirrup assembly snugly fitted about the lower leg above the ankle. The present invention includes a further improvement of a counter strap member just above the heel which further limits the side wall members from moving outward relative to the ankle. In addition, the present invention includes a fastening means to which the laces of the shoe may be attached thereby additionally compressing the lower portion of the side wall members. The lace fastening means cooperates with the counter strap so that each element counters the other to more properly immobilize the lower portion of the ankle brace. The combination of the fastening means for attaching the laces and the counter strap therefore provides for a significant improvement over the prior art ankle braces to more properly immobilize the ankle from undesired inversion and eversion. The use of the gel also provides for an improvement since it produces a foam dense foam material.

It should be appreciated that other types of high density foam materials may be used but he gel material is preferred since it may also have thermal properties to allow for the gel to be heated or cooled for added therapeutic effects.

BRIEF DESCRIPTION OF THE DRAWINGS

A clearer understanding of the present invention will be had with reference to the following description and drawings wherein.

DETAILED DESCRIPTION OF THE PREFERRED EMBODIMENT

Figure 1:
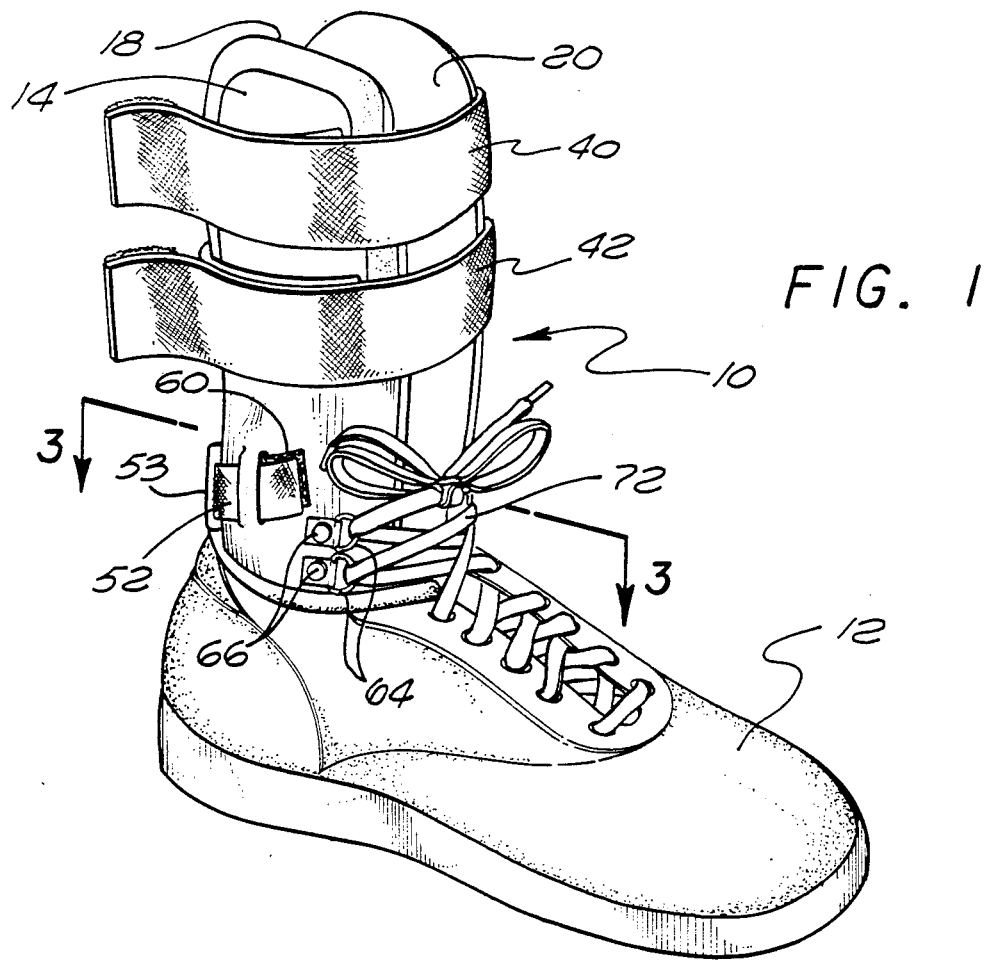
FIG. 1 is a perspective view of the ankle brace of the present invention fitted in association with a shoe including laces.
Figure 3:
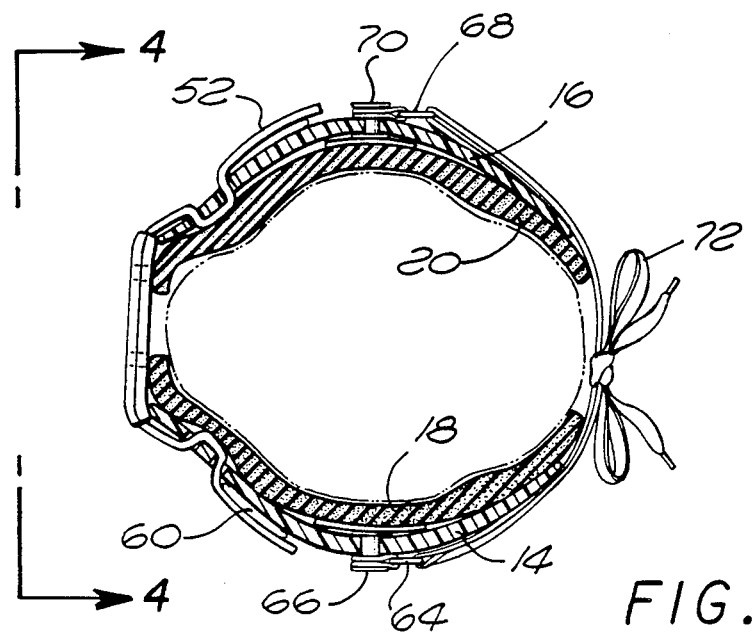
FIG. 3 is a cross sectional view of the ankle brace taken along lines 3—3 of FIG. 1.
Figure 2:
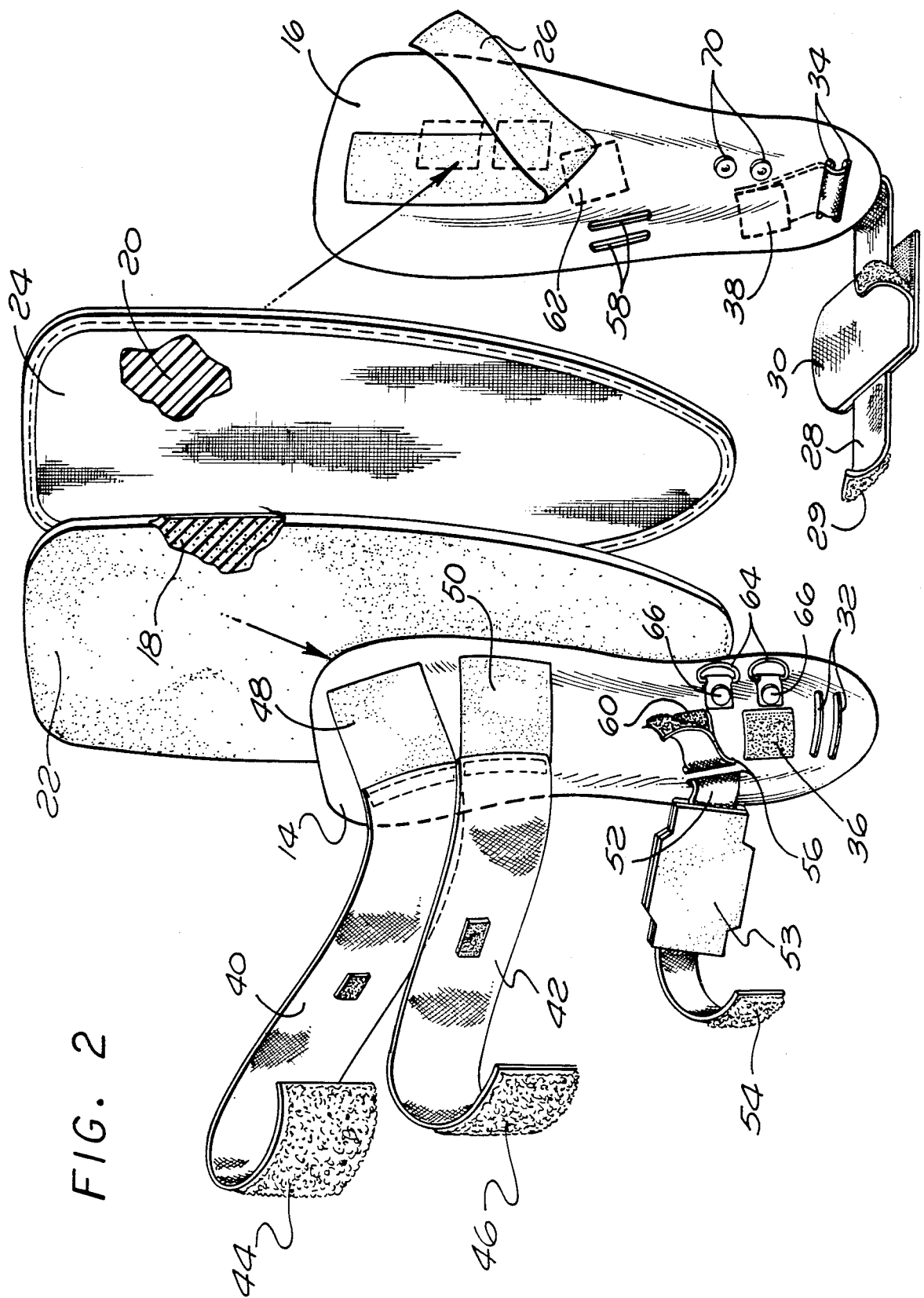
FIG. 2 is an exploded view of the various elements of the ankle brace.
Figure 4:
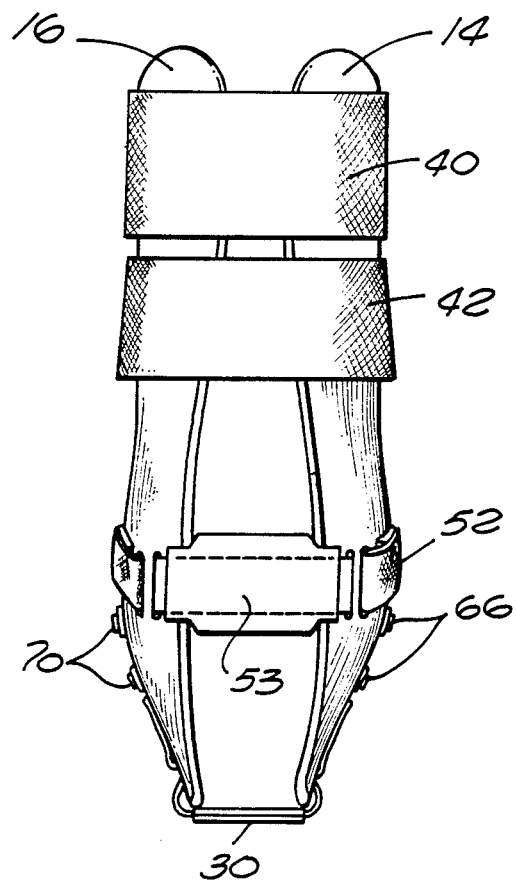
FIG. 4 is a back view of the ankle brace.
Figure 5:
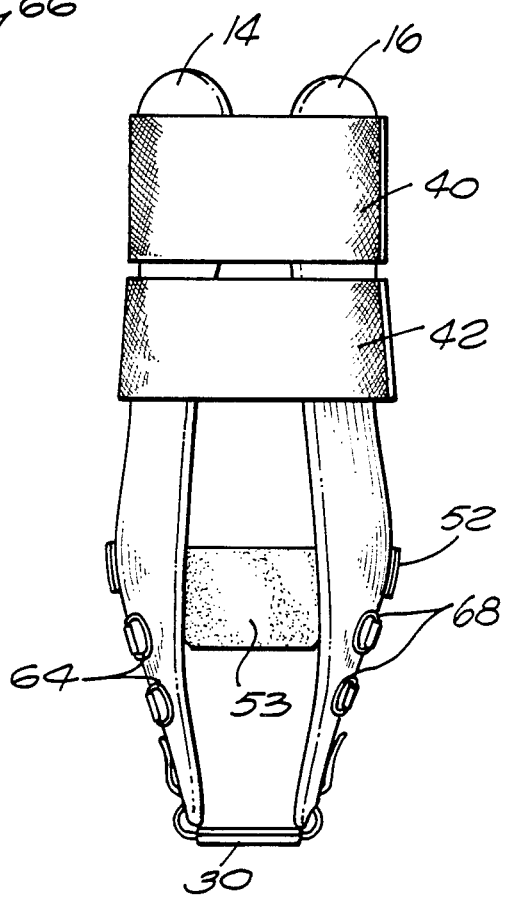
FIG. 5 is a front view of the ankle brace.

As shown in FIG. 1, an ankle brace 10 of the present invention is shown fitted within the shoe 12 of an injured person. Referring specifically to FIGS. 1 and 2, the ankle brace 10 is formed as a stirrup including a pair of side support members 14 and 16 made of rigid plastic which is typically vacuum formed to conform to the shape of the lower leg. Positioned within the side support members are resilient pad members 18 and 20 which are preferably formed of a dense material. Specifically, the resilient pad member 18 is shown to be a dense foam material and the resilient pad member 20 is shown to be a gel material. Of course, both pads would normally be formed of the same material but it is to be appreciated that different materials as well as combinations of gel and foam may be used to form the pads. In any event the resilient pads 18 and 20 provide for a cushion effect against the lower extremity of the lower leg and foot while at the same time firmly supporting the ankle.

If the material used is gel, then preferably the gel material may be of the patented type sold under the trademark ELASTO GEL by Southwest Technologies, Inc. of Kansas City, Missouri which patented gel material has thermal properties to allow the gel to be either preheated or cooled, so as to provide for added therapeutic effect. Even if the gel that is used does not have thermal properties, the dense gel material does provide for the desired flexibility and comfort. The gel material or dense foam is covered with a material 22 and 24, which material may be a fabric or plastic sheet to provide for additional comfort and may also absorb perspiration.

The resilient pads 18 and 20 may be attached to the inside of the side supports 14 and 16 using known means such as double sided adhesive 26 shown on side support 16 or some other attachment means such as velcro strips attached to the side supports and the pads. It is to be appreciated that side support 14 has a similar attachment means on its inside surface.

Interconnecting the two side supports 14 and 16 is a bottom strap 28 which includes a pad member 30. The bottom strap 28 may include a surface 29 of velcro material and with the bottom strap being adjustable through the use of double openings 32 and 34 in the side supports. The ends of the bottom strap 28 may be fixed in position with the use of additional velcro material 36 and 38 located on the outsides of the side support members 14 and 16. Specifically the adjustment is accomplished by positioning the ends of the strap 28 to extend from the outside of each side support member through a first one of the openings 32 and 34 and then back out through the other one of the openings 32 and 34 and then attached by the velcro material 36. The proper distance therefore may be easily adjusted between the side support members 14 and 16 at the lower most position.

The side supports may be also tightly attached around the leg just below the calf area using the two strap members 40 and 42. These strap members also include velcro portions on their outside surfaces, as shown by velcro material 44 and 46, and with velcro material 48 and 50 at the end portions of the straps. The velcro 48 and 50 is attached to the side supports 14 and 16. As shown in FIG. 1, these straps 40 and 42 may be tightly drawn around the leg and secured using the velcro material so that the upper portion of the ankle brace is tightly supported around the leg below or around the calf area.

With the prior art devices, one difficulty is the inability of the prior art ankle braces to properly immobilize the ankle. This can be seen since even with the bottom strap 28 and the upper straps 40 and 42, the two side support members 14 and 16 can easily twist and flex outward at the lower end of the ankle brace. The present invention overcomes this problem using a combination of structures.

Specifically the present invention includes a counter strap 52 located above the heel and with this counter strap similar to the bottom strap 28. Specifically the counter strap 52 includes a pad 53 and an inner surface of velcro material 54 and with the strap passing through double openings 56 in the side support 14 and double openings 58 in the side support 16. A further piece of velcro material 60 is attached to side support 14 and a piece of velcro material 62 is attached to side support 16. In this way the counter strap 52 may be adjusted in a similar manner to the bottom strap 28 to hold the back portion of the side support means 14 and 16 from twisting or flexing outward at the lower end of the ankle brace to compress the distal $\frac{1}{3}$ to $\frac{1}{2}$ of the brace.

In order to insure that the front portion of the side supports 14 and 16 to not twist or flex outward, the present invention includes fastening means provided on the side supports which cooperate with laces 72 of the shoe 12 to compress the distal $\frac{1}{3}$ to $\frac{1}{2}$ of the brace. Specifically as shown in the drawings, this fastening means may be D-rings which are riveted to the side supports. Specifically, side support 14 may include a pair of D-rings 64 attached by rivets 66. Side support 16 may include a similar pair of D-rings 68 attached by rivets 70.

It is to be appreciated that other attachment means may be used. For example, only a single D-ring may be used or the D-ring can be completely eliminated and the attachment of the laces may be through a hole or slot in the side support. In addition the attachment means may be adjustable in position or the attachment means may be incorporated with the counter strap 52. In any event, the attachment means is located adjacent the side supports and used in association with the laces 72 of the shoe 12 and with the laces laced through the fastening means and pulled tight and tied so as to stabilize and compress the digital $\frac{1}{3}$ to $\frac{1}{2}$ of the lower front portion of the side supports 14 and 16. This structure prevents the side supports in the lower portion from twisting and flexing outward to more properly stabilize the and compress ankle against inversion and eversion and anterior subluxation.

The operation of the ankle brace of the present invention would be as follows; if the resilient pads 18 and 20 are to provide heat or cold then they would be made of a gel material as described above and would have been previously heated or cooled using appropriate techniques. For example, cooling would normally be provided by placing the pads in a freezer. Heating would occur by using a micro wave oven. The pads would then be attached to the inside of the side supports 14 and 16 using the fastening means.

If the brace had been previously used, then the bottom strap 28 and counter strap 52 would already have been adjusted. If not, the wearer would position the side supports 14 and 16 and pads to both sides of the ankle and then after the side supports are properly positioned, the ankle brace would be held in place using the strap members 40 and 42. The bottom strap 30 would then be adjusted by peeling the velcro material 29 back from the corresponding velcro 36 on the side supports and pulling up both sides of the strap 28 until the bottom of the side supports is firmly in position. The ends of the strap 30 would then be pressed down on the velcro 36 to lock the strap in position Similarly, the counter strap 52 would be adjusted to pull the back lower end of the side supports together above the heel area.

The shoe would now be fitted over the entire ankle brace, as shown in FIG. 1, and the laces 72 laced through the D-rings or other fastening means located at the lower end of the side supports 14 and 16. The laces would then be pulled tight and tied, again as shown in FIG. 1, so that the ankle brace is firmly in position.

It can be seen therefore that the present invention provides for a structure that can secure the ankle brace tightly to the leg throughout its entire length. The upper portion of the brace is tightly secured by the upper straps 40 and 42. The bottom distance between the side supports is properly positioned using the bottom strap 28. The present invention also provides for the ankle area to be tightly secured using a counter strap 52 in association with the laces of the shoe which are attached through a fastening means such as a D-ring to provide for the complete securing for the ankle brace around the leg.

In this way, the shoelaces, after securing to the ankle brace, is brought towards the center of the ankle to pull the brace into the midline. This secures the brace tightly on to the foot in the ankle area. The present invention therefore achieves a more proper containment of the brace on the lower one third portion of the brace. The counter strap increases the effectiveness of the brace by insuring a continuous fit around the ankle at the lower extremity of the brace. The use of the firm material such as gel provides for added support and comfort. Although the use of a viscous gel is preferred, other types of dense foams such as polyurethane or PVC foam could be used.

Although the invention has been described with reference to a particular embodiment it is to be appreciated that other adaptations and modifications may be used. For example as indicated above fastening means other than a D-ring could be used, such as a hole or opening in the side supports. In addition, the fastening means may be adjustable and may also be provided as part of the counter strap. However, it is preferred to use laces so as to more properly immobilize the ankle portion.

The invention is only to limited by the appended claims.

I claim:

1. An ankle brace for insertion into a shoe with laces for immobilizing the ankle against inversion or eversion while permitting planter-flexion and dorsi-flexion, including,
  a pair of substantially rigid or stiff side supports having upper and lower ends, preformed to conform to the shape of the lower leg, for fitting about the lower leg on both sides and with the side supports having a configuration to encase both sides of the ankle and with the lower end of the side supports for insertion into the sides of the shoe, said side support members having a maximum outward extent at an intermediate point at the ankle;
  pad members formed of a flexible gel material located on the inner surface of each side support to form a cushion between the ankle and the side supports;
  means for removably securing said gel pads to said side supports;
  means for securing the side supports to firmly encase the ankle; and
  the securing means including a counter strap extending between the side supports at a lower position just above the heel near said intermediate point, and fastening means located on the side supports substantially at an elevation at or immediately below said intermediate point and substantially at the level of the ankle joint to receive the laces of the shoe so that the laces can be tightened and tied to immobilize the ankle against inversion or eversion or anterior subluxation while permitting planter-flexion and dorsi-flexion.

2. The ankle brace of claim 1 wherein the gel material has thermal properties capable of retaining heat or cold.

3. The ankle brace of claim 1 wherein the securing means additionally includes at least one top strap for securing the side supports together at a top position.

4. The ankle brace of claim 1 wherein the securing means additionally includes a bottom strap for extending between the side supports at a bottom position within the shoe.

5. The ankle brace of claim 6 wherein the bottom strap is adjustable to adjust the distance between the side supports at the bottom position.

6. The ankle brace of claim 1 wherein the counter strap is adjustable to adjust the distance between the side supports at the lower position just above the heel.

7. The ankle brace of claim 1 wherein the fastening means is formed of at least one D-ring on each side support to receive the laces.

8. The ankle brace of claim 7 wherein each D-ring is attached directly to the side support.

9. An ankle brace for insertion into a shoe for immobilizing the ankle against inversion or eversion while permitting planter-flexion and dorsi-flexion, including,
  a pair of substantially rigid or stiff preformed side supports for fitting about the lower leg on both sides and with the side supports having a configuration to encase both sides of the ankle and with the lower end of the side supports for insertion into the sides of the shoe,
  pad members formed of a cushioning flexible material located on the inner surface of each side support to form a cushion between the ankle and the side supports;
  means for securing the side supports to firmly encase the ankle; and
  the shoe includes laces, and the securing means includes straps extending between the side supports to hold said side supports together; and fastening means located on the side supports to receive the laces of the shoe so that the laces can be tightened and tied to immobilize the ankle.

10. An ankle brace for insertion into a shoe with laces for immobilizing the ankle against inversion or eversion while permitting planter-flexion and dorsi-flexion, including:
  a pair of substantially rigid or stiff preformed side supports for fitting about the lower leg on both sides and with the side supports having upper and lower ends, and having a configuration to encase both sides of the ankle and with the lower end of the side supports for insertion into the sides of the shoe, said side support members having a maximum outward extent at an intermediate point at the ankle;
  pad means formed of a conforming flexible material located on the inner surface of each side support for forming a firm supporting cushion between the ankle and the side supports,
  means for securing the side supports to firmly encase the ankle, and
  the securing means including a counter strap extending between the side supports at a lower position just above the heel near said intermediate point, and exposed fastening means located on the side supports substantially at an elevation at or immediately below said intermediate point and substantially at the level of the ankle joint to receive the laces of the shoe substantially horizontally from the shoe so that the laces can tightened and tied to immobilize the ankle against inversion or eversion or anterior subluxation while permitting planter-flexion and dorsi-flexion.

11. A combined ankle brace and shoe with laces for immobilizing the ankle against inversion or eversion while permitting planter-flexion and dorsi-flexion, including:
  a pair of substantially rigid or stiff preformed side supports for fitting about the lower leg on both sides and with the side supports having upper and lower ends, and front and rear sides, and having a configuration to encase both sides of the ankle and with the lower end of the side supports for insertion into the sides of the shoe, pad means formed of a conforming flexible material located on the inner surface of each side support for forming a firm supporting cushion between the ankle and the side supports, means for securing the side supports to firmly encase the ankle, the securing means including flexible means extending between the side supports to the rear thereof, for holding the rear sides of the side supports together, and exposed fastening means located on both of the side supports toward the front sides thereof at the level of the ankle joint for receiving the laces of the shoe which extend from the shoe and angle upward to said exposed fastening means so that the laces can be tightened and tied to immobilize the ankle against inversion or eversion or anterior subluxation while permitting planter-flexion and dorsi-flexion; and said laces securing said shoe onto the wearer's foot and also to said exposed fastening means.

* * * * *